United States Patent [19]

Terao et al.

[11] Patent Number: 4,939,274
[45] Date of Patent: Jul. 3, 1990

[54] HYDROXYBUTENOLIDE DERIVATIVES, PRODUCTION AND USE THEREOF

[75] Inventors: Shinji Terao; Minoru Hirata, both of Osaka, Japan

[73] Assignee: Takeda Chemical Industries, Ltd., Osaka, Japan

[21] Appl. No.: 390,230

[22] Filed: Aug. 7, 1989

Related U.S. Application Data

[63] Continuation of Ser. No. 84,176, Aug. 12, 1987, abandoned.

[30] Foreign Application Priority Data

Aug. 29, 1986 [JP] Japan .................................. 61-204832

[51] Int. Cl.$^5$ ............................................ C07D 307/62
[52] U.S. Cl. ...................................... 549/315; 549/314
[58] Field of Search ................................. 549/314, 315

[56] References Cited

U.S. PATENT DOCUMENTS

| | | | |
|---|---|---|---|
| 3,981,857 | 9/1976 | Habu et al. | 549/315 |
| 4,749,790 | 6/1988 | Paloms-Coil et al. | 549/315 |
| 4,780,549 | 10/1988 | Terao et al. | 549/315 |

FOREIGN PATENT DOCUMENTS

| | | | |
|---|---|---|---|
| 0086324 | 2/1982 | European Pat. Off. | 549/315 |
| 0133493 | 8/1983 | European Pat. Off. | 549/315 |
| 1920176 | 10/1970 | Fed. Rep. of Germany | 549/315 |
| 2729903 | 1/1978 | Fed. Rep. of Germany | . |
| 1404689 | 6/1964 | France | . |
| 2114571 | 8/1983 | United Kingdom | 549/315 |

OTHER PUBLICATIONS

Chemische Berichte, vol. 110, No. 9, Sep. 1977, pp. 3228–3230, E. Logemann et al., "Synthese von 3,5–Didodecyltetronsäuure durch Ozonolyse von 2,6–Didodecyl-3,5–dihydroxy-1,4–benzochinon".

Journal of Organic Chemistry, vol. 50, #2, 1/25/85, pp. 281–283, "Autoxidation of Micelle-Solubilized Linoleic Acid. Relative Inhibitory Efficiencies of Ascorbate and Ascorbyl Palmitate", Pryor et al.

Journal of the Chemical Society, Chemical Communication, No. 1, Jan. 3, 1979, ppo. 81–82, "Synthesis of 4–Substituted Tetronic Acids: Multicolanic Acid", S. C. M. Fell et al.

Journal of The Chemical Society, Perkin Transactions I, No. 8, Aug. 1985, pp. 1567–1576, "Synthesis of (E)- and (Z)-Pulvinones", A. C. Campbell et al.

Tetrahedron, vol. 42, No. 4, May 1986, pp. 1117–1122, "Native American Food and Medicinal Plants 7. Antimicrobial Tetronic Acids from Lamatium Dissectum", B. C. Vanwagenen et al.

Journal of The American Society, vol. 104, No. 14, Jul. 14, 1982, pp. 3923–3928, American Chemical Society, "Stereoselective, Biogenetically Patterned Synthesis of ($\pm$)-Aplysistatin", J. D. White et al.

Primary Examiner—Asok Pal
Attorney, Agent, or Firm—Wegner & Bretschneider

[57] ABSTRACT

The present invention relates to a compound of the formula:

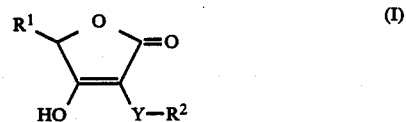

wherein Y is a chemical bond, oxygen atom, phenyleneoxy, or oxyphenyleneoxy; $R^1$ is hydrogen or hydrocarbon residue; and $R^2$ is hydrocarbon residue having two or more carbon atoms, production and use thereof.

The compound (I) of the present invention has an antioxidation activity and activities of preventing or improving functional disorders due to biologically active oxygen species, thus being useful as a pharmaceutical agent for prophylaxis and therapy of disorders in the circulatory system.

11 Claims, No Drawings

HYDROXYBUTENOLIDE DERIVATIVES, PRODUCTION AND USE THEREOF

This application is a continuation of Ser. No. 84,176 filed Aug. 12, 1987, now abandoned.

This invention relates to hydroxybutenolide derivatives useful for therapy, prophylaxis and improvement of disorders in the circulatory system, and a method of preparing them.

Diseases of heart, brain, kidney, etc., which are often observed in adults, are in most cases accompanied with ischemia as a basal pathologic state. The morbidity rate of, for example, ischemic heart diseases, ischemic cerebral diseases, ischemic renal disturbances and ischemic gastro-intestinal ulcers, has recently increased with the development of highly civilized society, and of the society holding high rates of persons of advanced age, and these diseases have become major factors in mortality rate in advanced countries.

Recently, it has been revealed that leukocyte and active oxygen species or reactive organic radical species play an important role in aggravation of lesions in ischemic tissues, i.e. lowering of cell function, disturbances, destruction and necrosis of cells [I. Fridovich, Annual Review of Pharmacology and Toxicology 23, 239 (1983); J. M. McCord, The New England Journal of Medicine, 312, 159 (1985); K. P. Burton, J. M. McCord and G. Ghai, American Journal of Physiology, 246, H776 (1984)]. As the biologically active oxygen species or reactive organic radical species in living system are considered, among others, superoxide ($O_2^-$), hydroxyl radical (.OH), singlet oxygen ($^1O_2$), and peroxide radical (ROO.). It is considered that, especially, abnormal oxygen-absorption and excess generation of superoxide being ($O_2^-$.) occurring when blood is reperfused again after once placed at the state of ischemia are causes of inviting disturbances on cells or tissues indiscriminately.

It has been known that superoxide dismutase effectively scavenges superoxide ($O_2^-$) and specifically protects against tissue damages and alleviates tissue disturbances after reperfusion of the site of ischemia or after ischemia [D. N. Granger, G. Rutili, J. M. McCord, Gastroenterology, 81, 82 (1981)]. Also, it has been reported that such compounds as ascorbic acid, α-tocopherol, cysteine and reduced glutathione have an activity to scavenge free radicals, and that these compounds could prevent lesions in tissues, which are supposedly caused by free radicals in certain pathological conditions [I. Fridovich, Science, 201, 875 (1978)].

Based on the biochemical and pharmacological fundamental studies so far made, revealing that active oxygen species and organic radical species play a significantly important role in causing tissue disturbances in a living system, especially those after reperfusion at the site of ischemic lesion in heart, brain, kidney, lung and digestive system, the present inventors have conducted research work for finding a novel type of pharmaceuticals excellent not only from the viewpoint of advantage of chemical synthesis but also pharmacologically as well as pharmaceutically aiming at scavenging active oxygen species and organic radical, as compared with the free radical scavengers mentioned above. As the result, the present inventors found that a certain type of hydroxybutenolide derivatives showed, as compared with ascorbic acid, α-tocopherol, etc., stronger actions to scavenge active oxygen species and organic radical species, and that they controlled ischemic heart diseases, disturbances in cerebral function or renal disorders, thus accomplishing the present invention.

The present invention provides a compound of the formula:

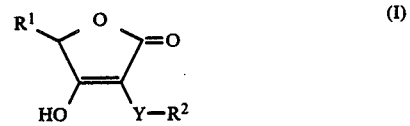

[wherein Y is a chemical bond, oxygen atom, phenyleneoxy or oxyphenyleneoxy; $R^1$ is hydrogen or a hydrocarbon residue; and $R^2$ is a hydrocarbon residue having two or more carbon atoms], and a method of preparing the compound [I], characterized by subjecting a compound of the formula:

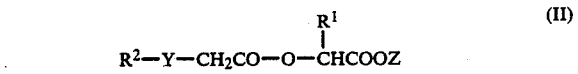

[wherein Y, $R^1$ and $R^2$ are of the same meaning as defined above, and Z is lower alkyl] to cyclization in the presence of a base.

In the above compound (I), as to phenyleneoxy and oxyphenyleneoxy for Y (spacer), o-, m- or p-phenyleneoxy and o-, m- or p-oxyphenyleneoxy may be respectively exemplified. Specifically preferable Y is chemical bond, o- or p-phenyleneoxy or oxygen atom.

The hydrocarbon residue shown by R: is exemplified by lower ($C_{1-6}$) alkyl, lower ($C_{2-6}$) alkenyl, lower ($C_{2-6}$) alkynyl, aryl, etc., and these groups may optionally be substituted.

The above-mentioned lower alkyl groups are exemplified by optionally substituted straight-chain or branched alkyl groups. The alkyl groups in the straight-chain or branched alkyl groups are exemplified by methyl, ethyl, propyl, isopropyl, n-butyl, n-pentyl, n-hexyl, etc. and preferably $C_1$–$C_3$ lower alkyl groups.

The above-mentioned lower alkenyl is preferably $C_2$–$C_4$ lower alkenyl, as exemplified by ethenyl, 1- or 2-propenyl, 1-,2- or 3-butenyl, etc.

The above-mentioned lower alkynyl is preferably $C_2$–$C_4$ lower alkynyl, as exemplified by ethynyl, 1- or 2-propynyl, 1, 2- or 3-butynyl, etc.

The above-mentioned aryl is exemplified by phenyl, naphthyl, etc.

These hydrocarbon residues may optionally be substituted by those groups, as exemplified by optionally substituted hydroxyl, $C_1$–$C_3$ lower alkylthio, optionally substituted phenylthio, optionally substituted phenyl, vinyl and optionally substituted ethynyl. As the substituents of the optionally substituted hydroxyl group are mentioned methyl, ethyl, n-propyl, isopropyl, allyl, propargyl, phenyl, etc.; as the substituents of the phenyl group of the optionally substituted phenylthio group and the optionally substituted phenyl group are mentioned a hydroxyl, methoxy, fluoro, etc.; and as the substituents of the optionally substituted ethynyl group are mentioned methyl, ethyl, phenyl, etc., respectively.

Especially preferable ones among the groups shown by $R^1$ include hydrogen atom, lower alkyl optionally substituted with a hydroxyl group or a carboxyl group and phenyl optionally substituted with a hydroxyl group or a carboxyl group.

Referring to $R^2$ in the compound (I), the hydrocarbon having two or more carbon atoms is exemplified by alkyl, alkenyl, alkynyl or aralkyl, and those of 6 to 20 carbon atoms are preferably. In the case of alkenyl or alkynyl, those having 1 to 4 unsaturated bonds(double or triple bond) are preferable.

The above-mentioned alkyl is exemplified by n-propyl, isopropyl, n-butyl, isobutyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, n-eicosyl, etc.

The above-mentioned alkenyl is exemplified by 7-hexadecenyl, 9-octadecenyl, 9,12-octadecadienyl, 9,12,15-octadecatrienyl, 8,11,14-eicosatrienyl, 5,8,11,14-eicosatetraenyl, etc.

The above-mentioned alkynyl is exemplified by 6-octynyl, 8-decynyl, 10-dodecynyl, 12-tetradecynyl, 14-hexadecynyl, 16-octadecynyl, etc.

Among these alkyl, alkenyl and alkynyl group, those having 9 to 20 carbon atoms are especially preferable.

The above-mentioned aralkyl is exemplified by benzyl, phenethyl, phenylpropyl, phenylbutyl, diphenylmethyl, 2,2-diphenylethyl, 1-naphthylethyl, 2-naphthylethyl, etc. and preferably phenyl-$C_{1-3}$alkyl.

The compound (I) of the present invention can be prepared by, for example, subjecting a compound (II) to cyclization in the presence of a base.

Examples of the above-mentioned base (basic condensing agent) include inorganic bases such as alkali metal hydrides (e.g. sodium hydride), organic metal bases such as organic alkali metals (e.g. potassium tertiary butoxide, lithium diisopropylamide), etc., and as the solvent are mentioned organic solvents such as alcohols (e.g. tertiary butanol), ethers (e.g. dioxane, tetrahydrofuran), amides (e.g. N,N-dimethylformamide, hexamethylphosphoramide), etc. The reaction temperature ranges from 0° C. to 70° C., and the reaction is completed in about 1 to 8 hours.

The starting compound (II) can be prepared by, for example, the following steps.

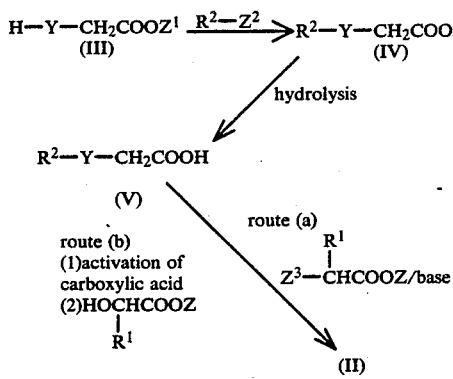

[wherein Y, Z, $R^1$ and $R^2$ are of the same meaning as defined above, $Z^1$ stands for lower alkyl, and $Z^2,Z^3$ stand for halogen respcetively].

The above-mentioned steps comprise allowing, for example, acetic acid ester (III) to react with halogenated hydrocarbon ($R^2$-$Z^2$) in the presence of a base to give a compound (IV), subjecting the compound (IV) to alkali hydrolysis to give a carboxylic acid derivative (V), then subjecting the compound (V) to esterification via the route (a) or (b) to give the intermediate compound (II).

In the above-mentioned steps, the base to be employed for the production of the compound (IV) is exemplified by potassium carbonate, sodium carbonate, sodium hydride, etc., and the solvent is exemplified by methanol, ethanol, dimethyl sulfoxide, N,N-dimethylformamide, dioxane, tetrahydrofuran, etc. The compound (IV) is subjected to alkali hydrolysis by conventional means, followed by rendering pH of the hydrolyzate to acidic to thereby obtain the free carboxylic acid derivative (V).

When the intermediate (II) is produced via the reaction route (a), the carboxylic acid derivative (V) is allowed to react with α-halogeno carboxylic acid ester in the presence of a base. The esterification is conducted by a conventional means, and the solvents and bases mentioned in the production of the compound (IV) can be likewise used. The intermediate (II) can also be produced via the route (b), more specifically, the carboxyl group of the compound (V) is activated by a per se conventional means, followed by allowing the resultant to react with α-hydroxycarboxylic acid in the presence of a base. The base and the solvent in this reaction step can be chosen from those exemplified in the above-mentioned production of the compound (IV).

Compounds (I) thus prepared can be isolated by per se conventional means (e.g. silica gel chromatography, recrystallization, etc.).

The compounds (I) of this invention show anti-oxidation action in the experiments in vitro employing brain homogenates of rats, and, in the ischemia-reperfusion model in the heart of rats or the ischemic brain model in rats or the renal failure model in rats due to oxygen free radicals; they show actions of preventing or improving the respective functional disorders, while they show remarkably low toxicity and very little side effects. The compound (I) of this invention shows therapeutic, prophylactic and improving actions against various functional disorders in mammals (e.g. mouse, rat, rabbit, dog, monkey, human, etc.), for example, ischemic heart diseases (arrhythmia, coronary vasospasm, necrosis of cardiac tissue, myocardial infarcation, etc.), subarachnoidal hemorrhage, ischemic disorders of cerebral tissue (e.g. cerebral infarction, dementia, etc.), ischemic renal disorders, ischemic intestinal disorders (e.g. intestinal ulcer, etc.), thus being useful as preventing and improving agents of functional disorders in the circulatory system.

Specific examples of the use as the above preventing and improving agents of functional disorders in the circulatory system include agents of anti-arrhythmia, anti-myocardiac infarction, anti-cerebral infarction, agents of preventing dementia, senile dementia, agents of therapy and improvement after subarachnoidal hemorrhage, improving agents of renal functions, therapeutic agents of stress,intestinal ulcer, etc.

The compounds of the present invention are of low toxicity (e.g. in an acute toxicity test in mice, no test animals were killed by oral administration of those compounds at a dose of 1000 mg/kg), and the compound (I) of the present invention can be safely administered orally or non-orally as pharmaceutical compositions [e.g. tablets, capsules (including soft-capsules and micro-capsules), liquids, suppositories, injections, preparations for nasal inhalation] prepared by mixing with per se conventional pharmacologically acceptable carriers, excipients, diluent, etc. in accordance with per se known methods. While the dosage varies with the subjects, administration routes, symptoms, etc., it is usually, when administered to the above-mentioned mammals, in terms of the compound (I), about 0.1 mg/kg to 50 mg/kg body weight, preferably about 0.5 mg/kg to 20 mg/kg body weight 1 to 3 times a day.

When the compound (I) is administered non-orally, for example, as a suppository, about 5 mg to 10 mg/kg in terms of the compound (I) is administered 1 to 2 times a day, and as an injection, about 0.1 mg/kg to 5 mg/kg in terms of the compound (I) is desirably used 1 to 2 times a day.

For preparation of the above-mentioned compositions for oral use, for example tablets, a binding agent (e.g. hydroxypropyl cellulose, hydroxymethylpropylmethyl cellulose, macrogol, etc.), a disintegrator (e.g. starch, carboxymethyl cellulose calcium, etc.), an excipient (e.g. lactose, starch, etc.), a lubricant (e.g. magnesium stearate, talc, etc.), etc. may be suitably incorporated.

When a composition for non-oral use, for example an injectable preparation, is prepared, an isotonizing agent (e.g. glucose, D-sorbitol, D-mannitol, sodium chloride, etc.), an antiseptic (e.g. benzyl alcohol, chlorobutanol, methyl para-hydroxybenzoate, propyl para-hydroxybenzoate, etc.), a buffer (e.g. phosphate buffer, sodium acetate buffer, etc.), etc. may be suitably incorporated.

EXPERIMENT 1

Activity to inhibit lipid peroxide formation in rat brain tissue homogenate:

(i) Method:

Male SD rats (12-week-old) were subjected to exsanguination under anesthesia with pentobarbital, then the brain was excised. The brain tissue was homogenized in a phosphate buffer (pH 7.4) to prepare a 5% homogenate. After incubation of the homogenate at 37° C. for 1 hour, the amount of lipid peroxides formed therein was determined by the thiobarbituric acid (TBA) method in accordance with the report of Ohkawa et al. on Analytical Biochemistry, 95, 351, (1979).

The test drug was added to the 5% homogenate before incubation so as to make the final concentration be $10^{-5}$M The activity to inhibit the formation of lipid peroxide was compared with that of the reference group to which was added the solvent (DMSO), and shown by % inhibition. (ii) The results are shown in Table 1.

TABLE 1

| Activities to inhibit lipid peroxide formation in rat brain tissue homogenates (TBA method) | |
|---|---|
| Compound | Inhibition rate (%)* |
| 4-a | 57.1 |
| 4-b | 100.0 |
| 4-c | 98.8 |
| 4-d | 100.0 |
| 4-e | 100.0 |
| 4-f | 89.7 |
| 4-g | 100.0 |
| 4-h | 100.0 |
| 4-i | 100.0 |
| 4-j | 100.0 |
| 4-k | 80.1 |
| Vitamin C | −71.6 |
| Vitamin E | 44.9 |

*Note
The concentration of each compound is $10^{-5}$ M, and the number of experiments is 3 with each compound. Inhibitory effects (%) are shown by mean values.

EXPERIMENT 2

Activity to inhibit occurrence of ventricular arrhythmia during coronary artery occlusion-reperfusion in rat hearts

(i) Method

Male SD rats (9- to 13-week old, 250 to 370 g) were used. The animals were subjected to thoractonomy under artificial respiration while anesthesia was maintained by administering pentobarbital. The left anterior descending coronary artery was ligated with silk thread for 5 minutes, then the ligation was released to allow reperfusion, and the animals were observed for 10 minutes. By recording standard limb lead II electrocardiograms, occurrence of ventricular arrhythmia was examined.

The animals were treated, under non-anesthesia, with test drugs as a gum arabic suspension at the dosage of 10 mg/kg at the time of about 180 minutes prior to closure of coronary artery The results are shown in Table 2.

(ii) Results

When reperfusion was permitted after the closure for 5 minutes of the left anterior descending coronary artery, ventricular arrhythmia, typically exemplified by occasionally occurring premature ventricular contractions (PVCs), ventricular tachycardia (VT) and ventricular fibrillation (VF), were observed. VT and VF were paroxysmally repeated, or sustained VF resulted in death.

In the group administered with the vehicle (control), VF and VT were observed in more than 90% of the animals, and the durations were respectively about 80 and 20 to 30 seconds. Among the animals, 10 to 25% were killed by occurrence of sustained VF.

In the group treated with 10 mg/kg of compound (4-c), occurrence of those types of arrhythmia was suppressed to a remarkably significant degree. Even when the arrhythmia occurred, the period of time during which the symptom lasted was shortened. Consequently, the mortality due to VF was low. Frequency of occasional PVCs was around 10 times/minute in the group of the vehicle, while, in the group administered with compound (4-c), the frequency was significantly less.

On the other hand, no significant effect was observed on oral administration of vitamin C or E at the dosage of 50 mg/kg.

Incidences of ventricular fibrillation and ventricular tachycardia are shown by the percentage of the number of animals presenting the symptoms relative to the number of animals subjected to the test, and the duration of the symptoms was shown in average ±SEM by seconds. Extrasystole is shown by the number of systole/min., and the mortality is shown by the percentage of the number of killed animals relative to the number of test animals.

TABLE 2

Effects on ventricular arrhythmias observed when reperfusion was permitted after closure of the coronary artery in rat hearts.

| Group | Ventricular fibrillation | | Ventricular tachycardia | | | |
|---|---|---|---|---|---|---|
| | Incidence (10 min.) | Duration (sec.) | Incidence (10 min.) | Duration (sec.) | Exrasystole (times/min.) | Mortality |
| Control | 4.1 ± 0.7 | 74.2 ± 30.8 | 11.5 ± 5.0 | 26.5 ± 6.8 | 11.0 ± 4.0 | 2/18 |
| Compound (4-c) (10 mg/Kg) | 1.3 ± 0.6 | 3.4 ± 2.9 | 2.0 ± 2.0 | 3.8 ± 3.8 | 1.2 ± 0.8 | 0/4 |
| Vitamin C 50 mg/kg | 5.4 ± 0.8 | 74.1 ± 36.0 | 9.5 ± 1.8 | 12.0 ± 2.9 | 11.0 ± 0.8 | 1/12 |
| Vitamin E 50 mg/Kg | 2.0 ± 0.7 | 43.4 ± 36.0 | 3.7 ± 1.5 | 22.3 ± 9.7 | 7.0 ± 4.1 | 1/10 |

EXPERIMENT 3

Acute toxicity in mice (i) Method

Male Crj-ICR mice (4-week-old, 21 to 26 g) were used. The animals, divided into groups, each consisting of six mice, were administered orally with compounds (4-c, 4-h) at the dosages of 300 and 1000 mg/kg, respectively. Then, each group was housed in a cage and observed for 24 hours.

The test drugs were suspended in gum arabic and administered at a volume of 0.1 ml/10 g.

(ii) Results

In both groups treated with compounds (4-c, 4-h) at the dosages of 300 and 1000 mg/kg, respectively, the state of sedation and ptosis were observed on half number of the test animals, but they had recovered within 3 hours. During 24-hour-observation, no test animals of either group were killed.

REFERENCE EXAMPLE 1

To a dimethylformamide (DMF, 100 ml) solution of ethyl 4-hydroxyphenyl acetate (18 g, 0.1 mol.) and dodecyl bromide (25 g, 0.1 mol.) was added potassium carbonate (15 g, 0.1 mol.). The mixture was stirred at 100° C. for one hour. To the reaction solution, after cooling, was added water (200 ml), which was subjected to extraction with isopropyl ether (IPE). The organic layer was washed with water, dried and concentrated under reduced pressure. The concentrate was dissolved in a mixture of methanol (100 ml) and tetrahydrofuran (THF, 100 ml). To the solution was added aqueous sodium hydroxide (10 g, 0.25 xol.), and the mixture was stirred at 50° C. The reaction solution was concentrated under reduced pressure, and the pH was adjusted to 4, followed by extraction with ethyl acetate. The organic layer was washed with water, dried and concentrated under reduced pressure to leave crude crystals Recrystallization from hexane-IPE gave 4-dodecyloxyphenylacetic acid (1-e, 20 g, 63%).

By the same procedure as above, compounds (1-a to 1-d and 1-f to 1-i) were synthesized. Physicochemical properties and NMR spectra of these compounds are shown in Table 3.

TABLE 3

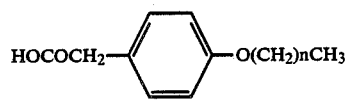

$HOCOCH_2-\text{C}_6\text{H}_4-O(CH_2)_nCH_3$

| Compd. | n | formula MP(°C.) | NMR spectrum (in CDCl$_3$, δ value: ppm) | yield (%) |
|---|---|---|---|---|
| 1-a | 4 | C$_{13}$H$_{15}$O$_3$ 75-76 | 7.17(2H, d, 9Hz), 6.85(2H, d, 9Hz), 3.92(2H, t, 7Hz), 3.56(2H, s), 1.76 (2H, m), 1.39(4H, s), 0.92(3H, m) | 53 |
| 1-b | 6 | C$_{15}$H$_{22}$O$_3$ 79-80 | 7.19(2H, d, 9Hz), 6.85(2H, d, 9Hz), 3.92(2H, t, 7Hz), 3.54(2H, s), 1.75(2H, m), 1.34(8H, m), 0.88(3H, m) | 89 |
| 1-c | 9 | C$_{18}$H$_{28}$O$_3$ 69-70 | 7.16(2H, d, 9Hz), 6.82(2H, d, 9Hz), 3.91(2H, t, 7Hz), 3.55(2H, s), 1.74 (2H, m), 1.26(14H, s), 0.87(3H, m) | 70 |
| 1-d | 10 | C$_{19}$H$_{30}$O$_3$ 85-86 | 7.17(2H, d, 9Hz), 6.83(2H, d, 9Hz), 3.91(2H, t, 7Hz), 3.54(2H, s), 1.70 (2H, m), 1.27(16H, s), 0.87(3H, m) | 75 |
| 1-e | 11 | C$_{20}$H$_{32}$O$_3$ 81-82 | 7.10(2H, d, 9Hz), 6.84(2H, d, 9Hz), 3.92(2H, t, 7Hz), 3.63(2H, s), 1.70 (2H, m), 1.29(18H, s), 0.87(3H, m) | 63 |
| 1-f | 13 | C$_{22}$H$_{36}$O$_3$ 84-85 | 7.16(2H, d, 9Hz), 6.82(2H, d, 9Hz), 3.90(2H, t, 7Hz), 7.54(2H, s), 1.70 (2H, m), 1.26(22H, s), 0.85(3H, m) | 71 |
| 1-g | 17 | C$_{26}$H$_{44}$O$_3$ 80-81 | 7.18(2H, d, 9Hz), 6.83(2H, d, 9Hz), 3.92(2H, t, 7Hz), 3.57(2H, s), 1.75 (2H, m), 1.25(30H, s), 0.88(3H, m) | 68 |

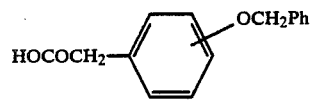

$HOCOCH_2-\text{C}_6\text{H}_4-OCH_2Ph$

| Compd. | position | formula MP(°C.) | NMR spectrum (in CDCl$_3$, δ value: ppm) | yield (%) |
|---|---|---|---|---|
| 1-h | o- | C$_{15}$H$_{14}$O$_3$ 94-95 | 7.33(7H, m), 6.92(2H, m) 5.04(2H, s), 3.68(2H, s) | 56 |
| 1-i | p- | C$_{15}$H$_{14}$O$_3$ | 7.37(5H, m), 7.17(2H, d, 7Hz) | 72 |

TABLE 3-continued

| | | |
|---|---|---|
| 116-117 | 6.91(2H, d, 7Hz), 5.21(2H, s), 3.53(2H, s) | |

REFERENCE EXAMPLE 2

To a DMF solution (30 ml) of 4-dodecyloxyphenylacetic acid (5.2 g, 16 mmol.) and ethyl bromoacetate (2.8 g, 20 mmol.) was added potassium carbonate (2.8 g, 20 mmol.) The mixture was stirred at 80° C. for one hour. The reaction solution was cooled, to which was then added water (100 ml), followed by extraction with IPE. The organic layer was washed with water, dried and concentrated under reduced pressure. The concentrate was purified by means of a silica gel chromatography (developing solvent: IPE) to give ethoxycarbonylmethyl 4-dodecyloxphenylacetate (2-h, 5.0 g, 82%).

By the same procedure as above, compounds (2-a to 2-c, 2-f, 2-j to 2-m) were prepared. Physico-chemical properties and NMR spectra of these compounds are shown in Table 4.

REFERENCE EXAMPLE 3

To a DMF solution (30 ml) of 4-dodecyloxyphenylacetic acid (2.4 g, 7.5 mmol.) and 2-bromopropionic acid (1.5 g, 8 mmol.) was added potassium carbonate (1.5 g, 10 mmol.). The mixture was stirred at 80° C. for 2 hours. The reaction solution was cooled, to which was added water (50 ml). The mixture was subjected to extraction with IPE. The organic layer was washed with water, dried and concentrated under reduced pressure. The concentrate was purified by means of a silica gel chromatography (developing solvent: IPE) to give 1-ethoxycarbonylethyl 4-dodecyloxyphenylacetate (2-i, 2.4 g, 76%).

By the same procedure as above, compound (2-d) was synthesized, whose physico-chemical properties and NMR spectrum are shown in Table 4.

REFERENCE EXAMPLE 4

To a dichloromethane (20 ml) solution of 4-undecyloxyphenylacetic acid (2 g, 7 mmol.) was added dropwise oxalyl chloride (1 ml). The reaction solution was stirred at 50° C. for one hour, which was then cooled, followed by concentration under reduced pressure The concentrate was dissolved in dichloromethane (10 ml), and the solution was added dropwise to a dichloromethane (10 ml) solution of methyl mandelate (1.1 g, 6.5 mmol.). To the reaction solution was added pyridine (2 ml), and the mixture was stirred at room temperature for two hours, to which was then added water (50 ml), followed by extraction with IPE. The organic layer was washed with water, dried and concentrated under reduced pressure. The concentrate was purified by means of a silica gel chromatography (developing solvent: IPE) to give methoxycarbonylphenylmethyl 4-undecyloxyphenylacetate (2-g, 1.4 g, 43%).

By the same procedure as above, compound (2-e) was synthesized. Physico-chemical properties and NMR spectra of these compounds are shown in Table 4.

TABLE 4

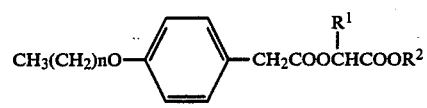

| Compd. | $R^1$ | $R^2$ | n | formula | NMR spectrum (in $CDCl_3$, δ value: ppm) |
|---|---|---|---|---|---|
| 2-a | H | Et | 4 | $C_{17}H_{24}O_5$ | 7.21(2H, d, 9Hz), 6.82(2H, d, 9Hz), 4.61(2H, s), 4.20(2H, q, 7Hz), 3.91(2H, t, 7Hz), 3.65(2H, s), 1.68(2H, m), 1.26(7H, m), 0.87(3H, m) |
| 2-b | H | Et | 6 | $C_{19}H_{28}O_5$ | 7.22(2H, d, 9Hz), 6.86(2H, d, 9Hz), 4.60(2H, s), 3.90(2H, s), 3.65(2H, s), 1.70(2H, m), 1.25(9H, m), 0.87(3H, m) |
| 2-c | H | Et | 9 | $C_{22}H_{34}O_5$ | 7.23(2H, d, 9Hz), 6.86(2H, d, 9Hz), 4.16(2H, q, 7Hz), 3.93(2H, t, 7Hz), 3.66(2H, s), 1.70(2H, m), 1.30(17H, m), 0.87(3H, m) |
| 2-d | Me | Et | 9 | $C_{23}H_{36}O_5$ | 7.19(2H, d, 9Hz), 6.85(2H, d, 9Hz), 5.65(1H, q, 7Hz), 4.20(2H, q, 7Hz), 3.92(2H, t, 7Hz), 3.61(2H, s), 1.70(2H, m), 1.26(17H, m), 0.86(3H, m) |
| 2-e | Ph | Me | 9 | $C_{28}H_{38}O_5$ | 7.41(5H, m), 7.22(2H, d, 9Hz), 6.85(2H, d, 9Hz), 5.94(1H, s), 3.92(2H, t, 7Hz), 3.68(3H, s), 1.77(2H, m), 1.27(14H, m), 0.87(3H, m) |
| 2-f | H | Et | 10 | $C_{23}H_{36}O_5$ | 7.20(2H, d, 9Hz), 6.86(2H, d, 9Hz), 4.61(2H, s), 4.20(2H, q, 7Hz), 3.90(2H, t, 7Hz), 3.66(2H, s), 1.70(2H, m), 1.26(19H, m), 0.85(3H, m) |
| 2-g | Ph | Me | 10 | $C_{29}H_{40}O_5$ | 7.40(5H, m), 7.21(2H, d, 9Hz), 6.86(2H, d, 9Hz), 5.95(1H, s), 3.66(3H, s), 1.70(2H, m), 1.27(16H, m), 0.86(3H, m) |
| 2-h | H | Et | 11 | $C_{24}H_{38}O_5$ | 7.20(2H, d, 9Hz), 6.86(2H, d, 9Hz), 4.61(2H, s), 4.19(2H, q, 7Hz), 3.92(2H, t, 7Hz), 3.66(2H, s), 1.70(2H, m), 1.25(21H, m), 0.87(3H, m) |
| 2-i | Me | Et | 11 | $C_{25}H_{40}O_5$ | 7.19(2H, d, 9Hz), 6.82(2H, d, 9Hz), 5.66(1H, q, 7Hz), 4.15(2H, q, 7Hz), 3.90(2H, t, 7Hz), 3.60(2H, s), 1.70(2H, m), 1.46(3H, d, 7Hz) 1.26(21H, m), 0.87(3H, m) |
| 2-j | H | Et | 13 | $C_{26}H_{42}O_5$ | 7.20(2H, d, 9Hz), 6.86(2H, d, 9Hz), 4.60(2H, s), 4.20(2H, q, 7Hz), 3.92(2H, t, 7Hz), 3.66(2H, s), 1.70(2H, m), 1.25(25H, m), 0.86(3H, m) |
| 2-k | H | Et | 17 | $C_{30}H_{50}O_5$ | 7.21(2H, d, 9Hz), 6.86(2H, d, 9Hz), 4.60(2H, s), 4.19(2H, q, 7Hz), 3.90(2H, t, 7Hz), 3.66(2H, s), 1.69(2H, m), 1.25(33H, m), 0.87(3H, m) |

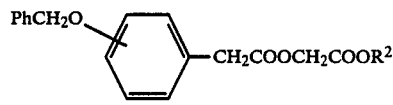

| Compd. | position | formula MP(°C.) | NMR spectrum (in $CDCl_3$, δ value: ppm) |
|---|---|---|---|
| 2-1 | o- | $C_{19}H_{20}O_5$ oil | 7.39(7H, m), 6.96(2H, m), 5.09(2H, s), 4.55(2H, s) 4.17(2H, q, 7Hz), 3.46(2H, s), 1.21(3H, t, 7Hz) |

TABLE 4-continued

| | | | |
|---|---|---|---|
| 2-m | p- | $C_{19}H_{20}O_5$ oil | 7.42(5H, m), 7.26(2H, d, 8Hz), 6.95(2H, d, 8Hz), 5.05(2H, s) 4.61(2H, s), 4.19(2H, q, 7Hz), 3.67(2H, s), 1.22(3H, t, 7Hz) |

REFERENCE EXAMPLE 5

In dimethylformamide (30 ml), ethyl glycolate (2.1 g) was allowed to react with 1-bromododecane (5.0 g) at 60° C. for 4 hours in the presence of potassium carbonate (2.8 g). To the reaction mixture was added water (100 ml), and the resultant mixture was subjected to extraction with IPE. The organic layer was washed with water and dried. The solvent was removed. The residue was subjected to hydrolysis with sodium hydroxide (4 g) for 2 hours in 20% aqueous methanol. The reaction solution was concentrated, and there was added water (50 ml), followed by washing with IPE twice. The aqueous layer was neutralized with 1N HCl, and the resulting precipitate was extracted with IPE. The extracted product was recrystallized from IPE-hexane to give dodecyloxyacetic acid (3-a, 4.3 g).

By the same procedure as above, compounds (3-b and 3-c) were synthesized. Physico-chemical properties and NMR spectra of these compounds are shown in Table 5.

REFERENCE EXAMPLE 6

In dimethylformamide (30 ml) were dissolved dodecyloxyacetic acid (4.3 g, 0.0176 mol.) and ethyl bromoacetate (2.94 g, 0.0176 mol.), and the reaction was allowed to proceed at 60° C. for 2 hours in the presence of potassium carbonate (2.4 g). To the reaction solution was added water (50 ml), and the resultant mixture was subjected to extraction with IPE. The aqueous layer was washed with water, dried and concentrated under reduced pressure. The concentrate was purified by means of silica gel chromatography [developing solvent: IPE-hexane (1:1)] to give compound (3-d, 5.1 g) as an oily product. By the same procedure as above, compounds (3-e to 3-f) were synthesized. Physico-chemical properties and NMR spectra of these compounds are shown in Table 5.

REFERENCE EXAMPLE 7

By the same procedure as that in Reference Example 5, stearic acid or oleic acid was allowed to react with ethyl bromoacetate to give the corresponding ester compounds (3-g and 3-h). (Table 6)

TABLE 6

| Compd. | Structure | formula | NMR spectrum (in $CDCl_3$, δ value:ppm) |
|---|---|---|---|
| 3-g | $Me(CH_2)_{15}CH_2COOCH_2$ COOEt | $C_{22}H_{42}O_4$ oil | 4.58(2H,s), 4.21(2H,q,7Hz), 2.41(2H,t,7Hz), 1.66 (2H,m), 1.23(31H,m), 0.87(3H,m) |
| 3-h | $Me(CH_2)_7CHCH(CH_2)_7$ COOCH$_2$COOEt | $C_{22}H_{40}O_4$ oil | 5.38(2H,m), 4.57(2H,s), 4.20(2H,q,7Hz), 2.40(2H,t, 7Hz), 1.94(4H,m), 1.66(2H,m), 1.26(25H,m), 0.87(3H,m) |

EXAMPLE 1

In a mixture of THF (50 ml) and DMF (10 ml) was dissolved ethoxycarbonylmethyl 4-dodecyloxyphenylacetate (5.0 g, 0.013 mol.). To the solution was added at room temperature potassium tertiary butoxide (2 g, 0.017 mol.). The mixture was stirred at room temperature for one hour, after which was added 2N HCl (20 ml). The resultant mixture was extracted with ethyl acetate. The organic layer was washed with water, dried and concentrated under reduced pressure The resultant crude crystals were recrystallized from IPE-ethyl acetate to give 2-(4-dodecyloxyphenyl)-3-hydroxy-2-buten-4-olide (4-h, 3.0 g, 70%). By a procedure analogous to the above, compounds (4-a to 4-c, 4-f, 4-j to 4-m) were synthesized. Physico-chemical properties and NMR spectra of these compounds are shown in Table 7.

EXAMPLE 2

In a mixture of THF (20 ml) and DMF (5 ml) was dissolved 1-ethoxycarbonylethyl 4-dodecyloxyphenylacetate. To the solution was added potassium tertiary butoxide (1.5 g, 0.012 mol.) at room temperature. The mixture was stirred at room temperature for one hour, and there was added 2N HCl(20 ml). The resultant mixture was extracted with ethyl acetate. The organic layer was washed with water, dried and concentrated under reduced pressure Resultant crude crystals were recrystallized from IPE-ethyl acetate to give 2-(4-methyl-2-buten-4-olide (4-i, 1.4 g, 67%). By the procedure analogous to the above, compounds (4-d, 4-g) were

TABLE 5

$Me(CH_2)nOCH_2COOR^1$

| Compd. | $R^1$ (n) | formula MP(°C.) | NMR spectrum (in $CDCl_3$, δ value:ppm) |
|---|---|---|---|
| 3-a | H (11) | $C_{14}H_{28}O_3$ 44–45 | 4.10(2H,s), 3.53(2H,t,7Hz), 1.61(2H,m), 1.27(18H,2), 0.85(3H,m) |
| 3-b | H (13) | $C_{16}H_{32}O_3$ 52–53 | 4.10(2H,s), 3.55(2H,t,7Hz), 1.62(2H,m), 1.25(22H,s), 0.88(3H,m) |
| 3-c | H (17) | $C_{20}H_{40}O_3$ 63–64 | 4.09(2H,s), 3.53(2H,t), 1.65(2H,m), 1.26(30H,s), 0.87(3H,m) |
| 3-d | $CH_2COOEt$ (11) | $C_{18}H_{42}O_5$ oil | 4.67(2H,s), 4.21(2H,q,7Hz), 4.18(2H,s), 3.54(2H,t,7Hz), 1.65(2H,m), 1.27(21H,m), 0.87(3H,m) |
| 3-e | $CH_2COOEt$ (13) | $C_{20}H_{38}O_5$ oil | 4.65(2H,s), 4.20(2H,q,7Hz), 4.17(2H,s), 3.55(2H,t,7Hz), 1.63(2H,m), 1.25(25H,s), 0.8(3H,m) |
| 3-f | $CH_2COOEt$ (17) | $C_{24}H_{49}O_5$ oil | 4.65(2H,s), 4.21(2H,q,7Hz), 4.15(2H,s), 3.53(2H,t,7Hz), 1.66(2H,m), 1.26(33H,s), 0.87(3H,m), | synthesized. Physico-chemical properties and NMR spectra of these compounds are shown in Table 7.

EXAMPLE 3

In a mixture of THF (10 ml) and DMF (1 ml) was dissolved methoxycarbonylphenylmethyl 4-undecyloxyphenylacetate (1.4 g, 3 mmol.). To the solution was added at room temperature potassium tertiary butoxide (1.5 g, 0.012 mol.) The mixture was stirred at room temperature for one hour, to which was added 2N HCl (30 ml), followed by extraction with ethyl acetate. The organic layer was washed with water, dried and concentrated under reduced pressure Resultant crude crystals were recrystallized from IPE-ethyl acetate to give 2-(4-undecyloxyphenyl)-3-hydroxy-4-phenyl-2-buten-4-olide (4-g, 0.9 g, 69%). Physico-chemical properties and NMR spectrum of this compound are shown in Table 7.

TABLE 7

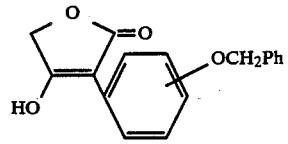

| Compd. | $R^1$ | n | formula MP(°C.) | NMR spectrum (in $D^6$-DMSO, δ value: ppm) |
|---|---|---|---|---|
| 4-a | H | 4 | $C_{15}H_{18}O_4$ 193-194 | 7.86(2H, d, 9Hz), 6.90(2H, d, 9Hz), 4.71(2H, s), 3.94(2H, t, 7Hz), 1.71(2H, m), 1.40(4H, m), 0.90(3H, m) |
| 4-b | H | 6 | $C_{17}H_{22}O_4$ 184-185 | 7.87(2H, d, 9Hz), 6.87(2H, d, 9Hz), 4.66(2H, s), 3.95(2H, t, 7Hz), 1.73(2H, m), 1.43(6H, m), 0.92(3H, m) |
| 4-c | H | 9 | $C_{20}H_{24}O_4$ 174-175 | 7.91(2H, d, 9Hz), 6.90(2H, d, 9Hz), 4.65(2H, s), 3.96(2H, t, 7Hz), 1.70(2H, m), 1.28(14H, s), 0.86(3H, m) |
| 4-d | Me | 9 | $C_{21}H_{30}O_4$ 149-150 | 7.83(2H, d, 9Hz), 6.91(2H, d, 9Hz), 4.90(1H, q, 7Hz), 3.95(2H, t, 7Hz), 1.68(2H, m), 1.46(3H, d, 7Hz), 1.27(14H, m), 0.85(3H, m) |
| 4-e | Ph | 9 | $C_{26}H_{32}O_4$ 160-161 | 7.89(2H, d, 9Hz), 7.41(5H, m), 6.92(2H, d, 9Hz), 5.81(1H, s), 3.95(2H, t, 7Hz), 1.69(2H, m), 1.26(14H, s), 0.85(3H, m) |
| 4-f | H | 10 | $C_{21}H_{30}O_4$ 176-177 | 7.85(2H, d, 9Hz), 6.85(2H, d, 9Hz), 4.64(2H, s), 3.93(2H, t, 7Hz), 1.70(2H, m), 1.27(16H, m), 0.86(3H, m) |
| 4-g | Ph | 10 | $C_{27}H_{32}O_4$ 132-133 | 7.67(2H, d, 9Hz), 7.26(5H, s), 6.85(2H, d, 9Hz), 5.53(1H, s), 3.88(2H, t, 7Hz), 1.70(2H, m), 1.28(16H, s), 0.86(3H, m) |
| 4-h | H | 11 | $C_{22}H_{32}O_4$ 172-173 | 7.86(2H, d, 9Hz), 6.84(2H, d, 9Hz), 4.65(2H, s), 3.95(2H, t, 7Hz), 1.70(2H, m), 1.28(18H, s), 0.85(3H, m) |
| 4-i | Me | 11 | $C_{23}H_{34}O_4$ 146-147 | 7.84(2H, d, 9Hz), 6.87(2H, d, 9Hz), 4.88(1H, q, 7Hz), 3.95(2H, t, 7Hz), 1.70(2H, m), 1.55(3H, d, 7Hz), 1.29(18H, s), 0.88(3H, m) |
| 4-j | H | 13 | $C_{24}H_{36}O_4$ 164-165 | 7.85(2H, d, 9Hz), 6.89(2H, d, 9Hz), 4.72(2H, s), 3.95(2H, t, 7Hz), 1.65(2H, m), 1.25(30H, s), 0.85(3H, m) |
| 4-k | H | 17 | $C_{28}H_{44}O_4$ 159-160 | 7.84(2H, d, 9Hz), 6.84(2H, d, 9Hz), 4.66(2H, s), 3.95(2H, t, 7Hz), 1.68(2H, m), 1.26(18H, s), 0.87(3H, m) |

| Compd. | position | formula MP(°C.) | NMR spectrum (in $D^6$-DMSO, δ value: ppm) |
|---|---|---|---|
| 4-l | o- | $C_{17}H_{14}O_4$ 135-136 | 7.38(7H, m), 7.04(2H, m), 5.11(2H, s) 4.68(2H, s) |
| 4-m | p- | $C_{17}H_{14}O_4$ 225-226 | 7.78(2H, d, 8Hz), 7.39(5H, m), 6.97(2H, d, 8Hz) 5.10(2H, s), 4.70(2H, s) |

EXAMPLE 4

By the same procedure as in Example 3, compounds (5-a to 5-e) were synthesized by using compounds (3-d to 3-h) synthesized in Reference Example 5 and 6. Physico-chemical properties and NMR spectra of these compounds are shown in Table 8.

TABLE 8

| Compd. | $R^2$ | formula MP (°C.) | NMR spectrum (in $D^6$-DMSO, δ value:ppm) |
|---|---|---|---|
| 5-a | Me(CH$_2$)$_{11}$O | $C_{16}H_{28}O_4$ 111-112 | 4.52(2H,s), 4.02(2H,t,7Hz), 1.65(2H,m), 1.24(18H, m), 0.85(3H,m) |
| 5-b | Me(CH$_2$)$_{13}$O | $C_{18}H_{32}O_4$ 112-113 | 4.57(2H,s), 3.92(2H,t,7Hz), 1.70(2H,m), 1.27(22H, m), 0.86(3H,m) |
| 5-c | Me(CH$_2$)$_{17}$O | $C_{22}H_{40}O_4$ 64-65 | 4.47(2H,s), 3.91(2H,t,7Hz), 1.70(2H,m), 1.25(30H), m), 0.85(3H,m) |

TABLE 8-continued

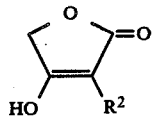

| Compd. | R² | formula MP (°C.) | NMR spectrum (in D⁶-DMSO, δ value:ppm) |
|---|---|---|---|
| 5-d | Me(CH₂)₇CH=CH(CH₂)₈ | C₂₀H₃₄O₃ 82–83 | 5.35(2H,m), 4.64(2H,s), 2.19(2H,m), 1.94(4H,m), 1.24(22H,m), 0.85(3H,m) |
| 5-e | Me(CH₂)₁₅ | C₂₀H₃₆O₃ 106–107 | 4.48(2H,s), 2.14(2H,t,7Hz), 1.25(28H,s), 0.87(3H,m) |

What is claimed is:

1. A compound of the formula:

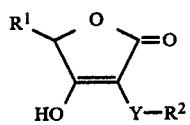

wherein Y is an oxygen atom, a phenyleneoxy, or an oxyphenyleneoxy;
$R^1$ is hydrogen, $C_{1-6}$ alkyl or phenyl unsubstituted or substituted with a hydroxy group or a carboxyl group; and $R^2$ is $C_{2-20}$ alkyl, $C_{2-20}$ alkenyl, or phenyl-$C_{1-3}$ alkyl.

2. The compound according to claim 1, wherein Y is an oxygen atom or ortho- or para-phenyleneoxy.

3. The compound according to claim 1, wherein $R^1$ is hydrogen, $C_{1-3}$ alkyl, or phenyl.

4. The compound according to claim 1, wherein $R^1$ is hydrogen.

5. The compound according to claim 1, wherein $R^1$ is phenyl.

6. The compound according to claim 1, wherein $R^2$ is $C_{6-20}$ alkyl or $C_{6-20}$ alkenyl.

7. The compound according to claim 1, wherein $R^2$ is $C_{9-20}$ alkyl, $C_{9-20}$ alkenyl or phenyl-$C_{1-3}$ alkyl.

8. The compound according to claim 1, wherein Y is ortho-or para-phenyleneoxy, $R^1$ is hydrogen and $R^2$ is $C_{9-20}$ alkyl or benzyl.

9. The compound according to claim 1, which is 2-(4-decyloxyphenyl)-3-hydroxy-2-buten-4-olide.

10. The compound according to claim 1, wwhich is 2-(4-benzyloxyphenyl)-3-hydroxy-2-buten-4-olide.

11. A pharmaceutical composition for therapy, prophylaxis or improvement of disorders in the circulatory system, which contains an effective amount of a compound according to claim 1 and a pharmaceutically acceptable carrier, excipient or diluent therefor.

* * * * *